United States Patent

Hammond et al.

[11] Patent Number: 5,763,884
[45] Date of Patent: Jun. 9, 1998

[54] SPECTROPHOTOMETRIC ANALYSIS

[75] Inventors: Stephen Victor Hammond, Folkestone; John Stephen Wakeman, Deal; David Grant Romans, St. Peters, all of England

[73] Assignee: Pfizer Inc., New York, N.Y.

[21] Appl. No.: 557,171

[22] PCT Filed: Jun. 16, 1994

[86] PCT No.: PCT/GB94/01298

§ 371 Date: Apr. 23, 1996

§ 102(e) Date: Apr. 23, 1996

[87] PCT Pub. No.: WO95/00831

PCT Pub. Date: Jan. 5, 1995

[30] Foreign Application Priority Data

Jun. 24, 1993 [GB] United Kingdom ............... 9313036

[51] Int. Cl.$^6$ ............... G01N 21/03; G01N 21/11
[52] U.S. Cl. ............... 250/339.11; 250/339.12; 250/341.8
[58] Field of Search ............... 250/339.11, 341.8, 250/339.12

[56] References Cited

U.S. PATENT DOCUMENTS

| 4,040,747 | 8/1977 | Webster ............... 356/418 |
| 4,640,614 | 2/1987 | Roberts et al. . |
| 4,692,620 | 9/1987 | Rosenthal . |
| 4,801,804 | 1/1989 | Rosenthal ............... 250/341.8 |
| 4,806,764 | 2/1989 | Satake . |
| 5,504,332 | 4/1996 | Richmond et al. ............... 250/339.12 |

FOREIGN PATENT DOCUMENTS

| 0240185 | 10/1987 | European Pat. Off. . |
| 92807 | 9/1972 | Germany . |
| 8700709 | 10/1988 | Netherlands . |
| 986445 | 3/1965 | United Kingdom . |

OTHER PUBLICATIONS

S. A. Yeboah et al., Applied Spectroscopy, vol. 38, No. 2, 1984, pp. 259–264.

F. Boroumand et al., Applied Spectroscopy, vol. 46, No. 12, 1992, pp. 1874–1886.

*Primary Examiner*—Constantine Hannaher
*Attorney, Agent, or Firm*—Peter C. Richardson; Gregg C. Benson

[57] ABSTRACT

A method of and apparatus for spectrophotometric analysis of a powder material by reflectance measurements of a near infrared beam has a sample cell 2 within which the powder 20A is compressed between a spring biased plate 13 and a window 8 to a predetermined density. Spectrophotometric analysis is effected on the powder 20A through the window 8 by scanning with the infrared beam over an area of the powder 20A which when multiplied by the density of the powder and the depth of penetration of the beam is consistent with a predetermined dosage weight—such as that at which the powder may be marketed.

20 Claims, 2 Drawing Sheets

SPECTROPHOTOMETRIC ANALYSIS

TECHNICAL FIELD & BACKGROUND ART

The present invention relates to spectrophotometric analysis and is particularly concerned with a method of, and apparatus for, such analysis of a material in powder form by reflectance measurements of a beam of electromagnetic radiation (usually near infrared) through the material.

Scanning spectrophotometers are well known to provide quantitative and qualitative analysis of organic and biological substances and materials and especially pharmaceutical materials in powder form. Typical near infrared scanning spectrophotometers are sold under the Trade Marks "COMPSCAN" by the Gardner Neotech Division of Pacific Scientific and "Model 6500" by NIR Systems Inc., and an example of such a spectrophotometer is disclosed in U.S. Pat. No. 4,692,620. Generally such known spectrophotometers comprise a cell within which a sample of the material for analysis is retained, a beam of electromagnetic radiation, usually near infrared as previously mentioned, which scans the material in the cell, and sensors which are responsive to reflections from the material and provide an output from which the analysis is effected. An example of a spectrophotometric cell which compresses the material contained therein is disclosed in Patent NL-A-8700709. Usually the spectrophotometer is coupled to a computer by which the scanning is controlled and which provides a required analysis of the output from the sensors.

Spectrophotometers of the kind discussed above are employed in the pharmaceutical industry for analysis of pharmaceutical materials in powder form, typically for carrying out random tests on samples of a pharmaceutical (which may be in, or rendered to, powder form) and as is intended to be marketed. These tests are principally to ensure that the material has the required chemical constituents, that the proportions of the required chemical constituents are correct and that the chemical constituents are dispersed uniformly throughout the material. The necessity to ensure that a pharmaceutical material has the correct chemical constituents in the required proportions is an understandable requirement. The requirement to ensure that the chemical constituents are uniformly distributed throughout the material is now called for by many regulatory authorities, such as the Medicines Control Agency in the United Kingdom, the U.S. Federal Drug Administration and the European Medical Commission. Many pharmaceuticals as supplied for use in a predetermined dosage weight, either in powder (for example capsule) or tablet form, contain a significant proportion of an inactive carrier substance or placebo through which the active chemical constituents are distributed. It is a requirement that the active chemical constituents are uniformly and evenly distributed throughout the carrier substance for each intended dose. With the aforementioned spectrophotometric random testing, spectral analysis of a pharmaceutical sample by conventional techniques has, on occasion, found to be unreliable in determining the distribution of the active chemical constituents; for example such tests may provide a false indication of the distribution when related to a dose weight of the pharmaceutical product as it is intended to be marketed or may be unacceptable to the regulatory authorities as having been carried out on an unrepresentative sample of the product when related to the intended dose weight. It is an object of the present invention to provide a method of and apparatus for spectrophotometric analysis of a material in powder form by reflectance measurements which is an improvement in known spectrophotometric apparatus and methods of analysis and may be used to alleviate the aforementioned problem in determining the distribution of the chemical constituents in the material so that such determination is consistent with a predetermined or intended dose by weight of the material.

STATEMENTS OF INVENTION & ADVANTAGES

According to the present invention there is provided a method of spectrophotometric analysis of a material by reflectance measurements of a beam of electromagnetic radiation through the material in powder form which comprises compacting the powder material to a predetermined density, determining the penetration depth of said beam in the compacted material and scanning the compacted powder material by the beam of electromagnetic radiation over an area and through a depth of the compacted material which when multiplied by the density of that powder material provides an analysis of a sample of the material which sample is representative of a desired predetermined dose by weight of the material.

Further according to the present invention there is provided apparatus for use in the method as specified in the immediately preceding paragraph which comprises a sample cell for retaining the powder material during said analysis, means for compacting and maintaining the powder material compacted in the sample cell to a predetermined density, and analysis control means for effecting relative displacement between the beam and the cell for scanning said compacted material by the beam and providing an analysis of the material over a predetermined area and through a predetermined depth of the material the product of which predetermined area, depth and density is consistent with a predetermined dose by weight of the material.

The present invention was primarily developed for the analysis of composite pharmaceutical materials using near infrared spectrophotometers and, for convenience, such use will be discussed hereinafter. It will however be appreciated that the invention is applicable to the analysis of materials in powder form other than pharmaceuticals and that electromagnetic radiation of a wave length other than near infrared may be employed in the development of the reflectance measurements from the powder material.

When a given pharmaceutical material in powder form (or reduced to powder form) is lightly compacted and subjected to photometric analysis, the penetration depth of the near infrared beam will vary depending upon the density of the powder. This penetration depth may be determined without difficulty experimentally for a given powder material which is compacted to a particular density (which may also be determined without difficulty). For example a typical penetration depth of approximately 0.5 millimeters may be expected for a near infrared beam in a pharmaceutical powder compacted to a density of 0.5 milligrams per cubic millimeter. By the present invention the powder which is to be subjected to analysis is compacted to a predetermined density for which the penetration depth of the near infrared beam is known and the powder is scanned by the beam for analysis over a predetermined area and through a predetermined depth of the powder. The product of this predetermined area and depth is controlled so that when multiplied by the density of the compacted powder, a weight of powder material results which is consistent with a predetermined dose weight at which the particular pharmaceutical may be intended to be marketed (for example as a tablet or as an encapsulated powder). Usually the actual thickness of the compacted powder will be greater than the penetration depth of the beam and in such case the area of the powder scanned multiplied by the penetration depth and the density of the compacted powder should equal the intended dose weight. It is however possible that the thickness of the compacted powder will be less than the penetration depth in which case the area scanned will be increased to compensate for the reduced thickness so that such area multiplied by the actual thickness of the powder material (assuming that the powder layer is of uniform or constant thickness) and the density of the powder material will equal the predetermined dosage weight. By this technique therefore the pharmaceutical powder can be subjected to qualitative and/or quantitative and/or constituent distribution analysis throughout a volume of the compacted powder which when multiplied by the density of that powder will be consistent with a predetermined dose by weight of the pharmaceutical material as it may be intended to be supplied for use. Such analysis should therefore satisfy regulatory requirements for ensuring that the active chemical constituents in the pharmaceutical material will (statistically on a random test basis) be distributed uniformly and evenly throughout a predetermined dose by weight at which the pharmaceutical material may be intended to be supplied. The necessary programming and control of the spectrophotometer for analysis of the compacted powder material (usually with the aid of a computer linked to the spectrophotometer) will be readily apparent to persons familiar with conventional spectrophotometric analysis techniques and having an understanding of the present invention and as such need not be discussed in detail herein.

The pharmaceutical powder under analysis will usually be retained in a sample cell which may be displaced relative to a stationary near infrared beam of predetermined width and this displacement is controlled so that the powder in the cell is scanned over a predetermined area. The sample cell in accordance with the present invention will differ from known cells by the provision of means for compacting the powder material against a window (which will usually be a flat sheet) through which scanning is to be effected and which maintains the material under a predetermined compaction (at which compaction the density of the powder material will be determined as will the penetration depth of the near infrared beam). Preferably the sample cell will have a hollow body, conveniently in the form of a trough, having a chamber with the window through which scanning is to be effected located in a base or side wall of the chambers. The compacting means for the powder may be in the form of a pressure plate which is received in the chamber and resiliently biased relative to the cell body so that the powder material is compacted between the window and the pressure plate. The plate will usually be resiliently biased by spring means. For example the pressure plate may be carried by a closure plate relative to which it is resiliently biased and the closure plate may be removably secured to close the chamber.

The transverse width of the infrared scanning beam and also the longitudinal extent of the scan will usually be adjustable on the spectrophotometer for varying the area of the compacted powder material which is scanned as is appropriate for a particular pharmaceutical material, density of compacted powder and actual penetration depth of the near infrared beam so that the required analysis is consistent with the predetermined dose by weight in which the pharmaceutical material may be supplied.

DRAWINGS

One embodiment of the present invention as applied to the spectrophotometric analysis of a pharmaceutical material or product provided in, or reduced to, powder form will now be described, by way of example only, with reference to the accompanying illustrative drawings in which.

DETAILED DESCRIPTION OF DRAWINGS

Figure 7:
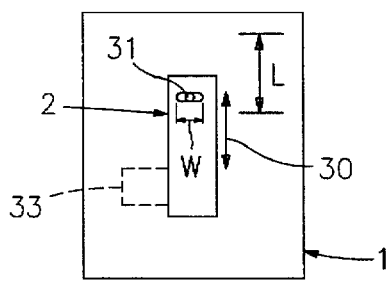

For the purpose of analysing pharmaceutical powder a spectrophotometer unit 1 (FIG. 7) is provided of generally known form, for example as sold under the Trade Mark MODEL 6500 by NIR Systems Inc., and fitted to which is a sample cell 2 in which is retained the powder that is to be subjected to analysis by reflective measurements of a near infrared beam.

The sample cell 2 comprises a longitudinally extending trough-shaped body 3 (which will usually be of metal) having a base 4 upwardly extending from which are a pair of parallel and opposed longitudinally extending side walls 5 and a pair of parallel and opposed laterally extending end walls 6. A longitudinally extending aperture 7 is provided in the base. Fitted over the base 7 is a flat sheet window 8 typically formed by transparent quartz. The window 8 together with the upstanding side and end walls form an elongated rectangular chamber 9.

Figure 5A:
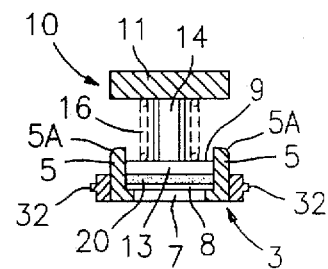
FIG. 5A is a lateral section showing fitment of the head in FIG. 5 to the body of FIG. 2.
Figure 5:
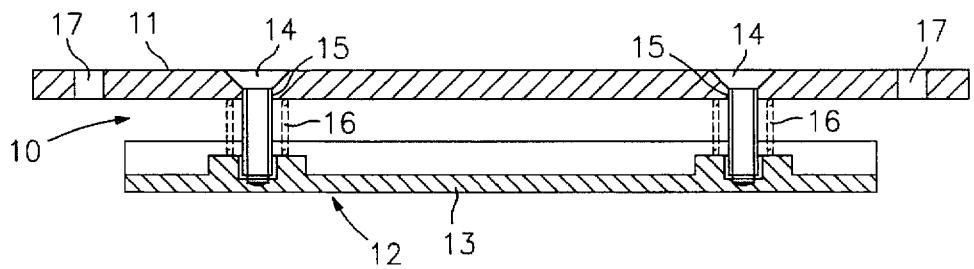
FIG. 5 is a side elevation of a head for the sample cell which head carries a pressure plate and is for attachment to the body of FIG. 2.

The sample cell 2 also has a head 10 (FIG. 5) which will usually be of metal and comprises a closure plate 11 that carries a compator 12 which is resiliently biased relative to the closure plate. The compactor 12 is formed by a flat elongate rectangular pressure plate 13 which is coupled to the closure plate 11 by bolts 14 each of which is axially slidable through respective apertures 15 in the closure plate. Retained on the shanks of the bolts 14 are helical springs 16 which react between the closure and pressure plates 11 and 12 to bias those plates away from each other in parallel relationship and to an extent permitted by heads of the bolts engaging with the closure plate 11. It will be apparent that the pressure plate 13 is displaceable relatively towards the closure plate 11 against the biasing of the springs 16 as the shanks of the bolts 14 slide through the apertures 15. The pressure plate 13 is receivable as a close sliding fit within the chamber 9 (as shown in FIG. 5A) and in such condition the head 10 may be secured to the body 3 by bolts (not shown) extending through apertures 17 in the closure plate 11 and engaging in threaded bores 18 in the body 3.

Figure 1:
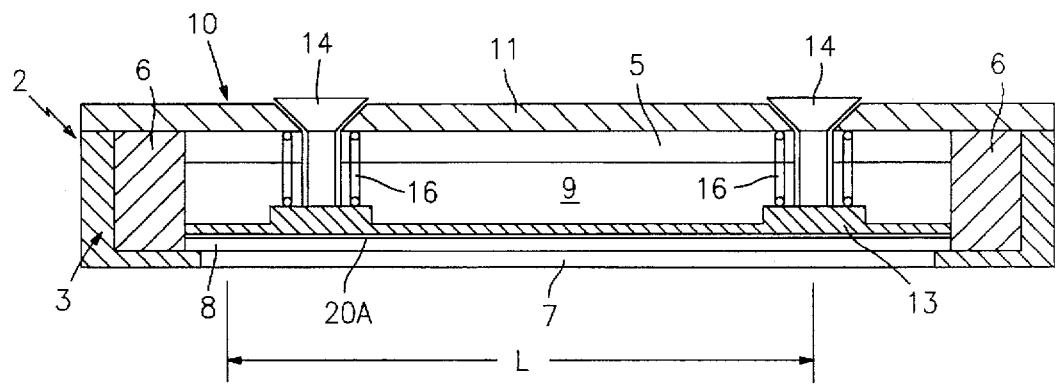
FIG. 1 is a longitudinal section of a sample cell containing the powder and prepared for analysis in a spectrophotometer.
Figure 2:
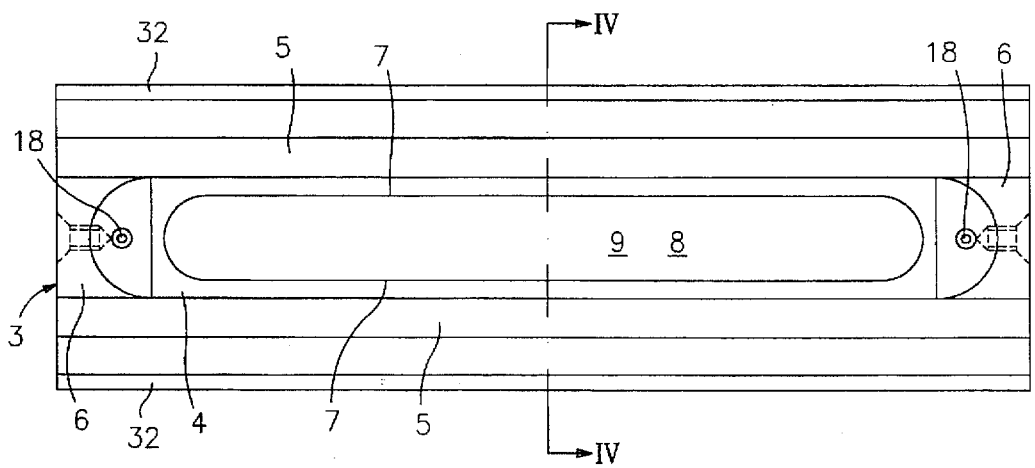
FIG. 2 is a plan view of a trough-shaped body for the sample cell in FIG. 1.
Figure 3:
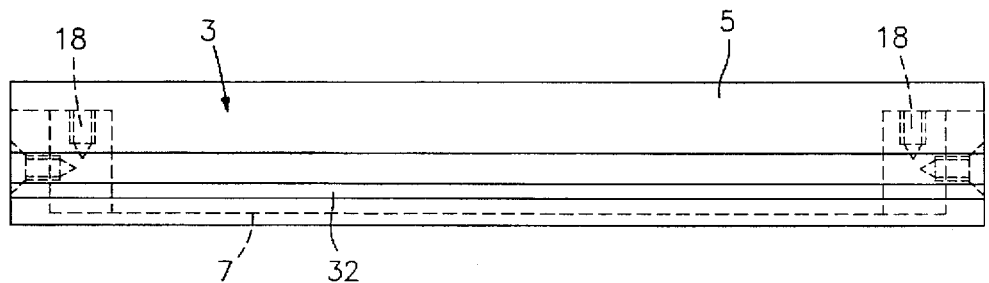
FIG. 3 is a side elevation of the body in FIG. 2.
Figure 4:
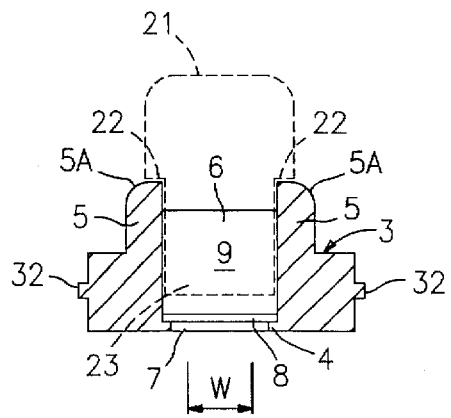
FIG. 4 is a lateral section of the body taken on the line IV—IV of FIG. 2.
Figure 6:
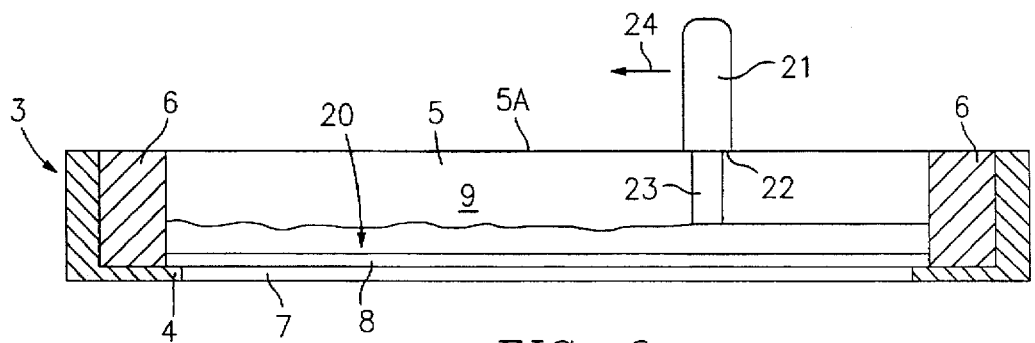
FIG. 6 is a longitudinal section of the body in FIG. 2 (similar to the view in FIG. 1) and shows preparation of the sample cell with the pharmaceutical powder for analysis, and FIG. 7 diagrammatically illustrates the front elevation of a spectrophotometer to which is fitted the sample cell shown in FIG. 1.

To prepare the sample cell 2 for use, and with the head 10 removed from the cell, the chamber 9 is charged with a predetermined weight of the pharmaceutical material 20 in powder form. The powder material 20 is then spread on the flat sheet of the window 8 to provide a parallel layer of predetermined thickness. Such spreading of the powder 20 is conveniently achieved as shown in FIG. 6 by use of a probe 21 (see also FIG. 4) having shoulders 22 which slide on and along upper edges 5A of the side walls 5 while an extension wall 23 of the probe projects into the cavity for a predetermined depth and to be closely and slidably received between the opposed side walls 5 (as indicated in FIG. 4). By displacing the probe 21 longitudinally through the chamber 9 in the direction indicated by arrow 24 in FIG. 6, the powder material 20 may be levelled on the window 8 to a uniform layer of constant predetermined thickness. The head 10 is now fitted to the body 3 as previously described. As the pressure plate 13 is slidably and closely received within the chamber 9 (see FIG. 5A) that plate lightly compacts the layer of powder 20 between itself and the window sheet 8 to the condition shown in FIG. 1. During this compaction it will be appreciated that the springs 16 will be compressed to provide a required compacting pressure on the powder when the closure plate 17 is bolted to the body 3. By initially charging the cell with a predetermined weight of powder material the volume of which is known, the density of the compacted layer of powder material 20A shown in FIG. 1 may readily be determined; furthermore, these characteristics for the compacted layer can be reproduced without difficulty for analysis of further test samples of the relevant powder.

The compacted powder 20A is to be subjected to analysis by scanning with, and reflective measurements from, a near infrared beam to which the powder is subjected through the aperture 7 and window 8. For this purpose the prepared sample cell 2 is fitted to the spectrophotometer unit 1 as shown generally in FIG. 7 to be reciprocated longitudinally (as indicated by the arrows 30) over the near infrared beam indicated at 31. Conveniently the body 3 of the sample cell has longitudinally extending outer side rails 32 by which the cell is retained in and slidable along tracks (not shown) in the spectrophotometer for its longitudinal displacement by a motorised drive indicated at 33.

For a given compacted pharmaceutical powder 20A in the sample cell 2, a near infrared beam of particular wavelength from the spectrophotometer will penetrate the compacted powder to a substantially constant depth (the penetration depth) which may readily be determined by experiment and this penetration depth is accordingly determined.

Conventionally pharmaceutical materials are marketed in individual predetermined dose weights, usually the dose weight is available in the form of a tablet (which may be rendered to powder) or as an encapsulated powder. In accordance with the present invention and having predetermined a required dose weight for the pharmaceutical material, the spectrophotometric analysis is controlled by scanning with the near infrared beam through a volume of the compacted powder material 20A in the sample cell which volume when multiplied by the density of the compacted powder is substantially equal to the predetermined dose weight. This analysis, which will usually be controlled by a computer (not shown) linked to the spectrophotometer 1, results from reflective measurements of the near infrared beam on the compacted powder 20A through the window 8 as detected by sensors in the unit 1 and may determine, inter alia, that the predetermined dose weight of the pharmaceutical powder has the correct and required chemical constituents and/or has its chemical constituents in the correct and required proportions and/or that the chemical constituents are distributed uniformly or evenly throughout the powder.

Usually the pharmaceutical powder 20A in the sample cell will be compacted to a depth greater than the penetration depth of the near infrared beam in which case the analysis is controlled so that the area of the compacted powder which is scanned by the beam multiplied by the density of the compacted powder and by the full depth of beam penetration is equal to the required dose weight. It is possible however for the uniform thickness layer of compacted powder 20A to have a depth or thickness less than that of the penetration depth for the infrared beam, in such case the analysis is controlled so that the area of the compacted powder 20A scanned by the beam multiplied by the density of the compacted powder and by the thickness of the compacted powder layer is equal to the required dose weight. For the purpose of such controlled area scanning, the transverse width W of the near infrared beam 31 (FIGS. 4 and 7) and the longitudinal extent of stroke L for displacement of the sample cell over the beam 31 will usually be adjustable.

In a typical example the pharmaceutical powder 20A may be compacted to a density of 0.5 milligramms per cubic millimeter in a layer of 1.0 millimeter thickness on the flat sheet window 8. For such powder material a typical penetration depth of a near infrared beam with a given wavelength is 0.5 millimeters. With these parameters and assuming that a predetermined dose weight for the pharmaceutical material in tablet form is 300 milligrammes, the required analysis may be effected by scanning the compacted powder with the width W of the beam 31 set at 20 millimeters and the length of stroke L of the compacted powder over the beam set at 60 millimeters.

We claim:

1. A method of spectrophotometric analysis of a material by reflectance measurements of a beam of electromagnetic radiation through the material in powder form which comprises compacting the powder material to a predetermined density, determining the penetration depth of said beam in the compacted material and scanning the compacted powder material by the beam of electromagnetic radiation over an area (W, L) and through a depth of the compacted material which when multiplied by the density of that powder material provides an analysis of a sample of the material which sample is representative of a desired predetermined dose by weight of the material.

2. A method as claimed in claim 1 in which the electromagnetic radiation is near infrared.

3. A method as claimed in claim 1 which comprises analysing the powder material for said predetermined dose weight and determining that at least one of (a) chemical constituents are present in the powder material as required, (b) chemical constituents in the powder material are present in required proportions and (c) chemical constituents required in the powder material are uniformly distributed throughout said material.

4. A method as claimed in claim 1 in which the material is a pharmaceutical and the predetermined dose weight is consistent with the weight of the pharmaceutical as is intended to be supplied in tablet or encapsulated powder form.

5. A method as claimed in claim 1 which comprises compacting the powder material to said predetermined density against a window through which said scanning is effected and maintaining said compaction during the scanning.

6. A method as claimed in claim 5 which comprises charging a chamber having said window with a predetermined volume of the powder material, spreading the powder material over the window to a predetermined depth and compacting the powder material against said window to provide a layer of said compacted material of predetermined density.

7. A method as claimed in claim 6 in which said layer of compacted material has a thickness greater than the said penetration depth of the beam.

8. A method according to claim 1 which comprises scanning the compacted powder material by displacement of that material in a longitudinal direction (L) relative to said beam which beam has a width (W) extending laterally and adjusting said beam width (W) and said longitudinal displacement (L) to provide said area over which the compacted powder material is scanned.

9. Apparatus for spectrophotometric analysis of a material by reflectance measurements of a beam of electromagnetic radiation through the material in powder form which comprises a sample cell for retaining the powder material during said analysis, means for compacting and maintaining the powder material compacted in the sample cell to a predetermined density, means providing said beam of electromagnetic radiation and for providing relative displacement between said beam and said compacted powder material in said sample cell, and analysis control means for effecting said relative displacement between the beam and the cell for scanning said compacted material by the beam and providing an analysis of the material over a predetermined area (W, L) and through a predetermined depth of the material the product of which predetermined area, depth and density is consistent with a predetermined dose by weight of the material.

10. Apparatus according to claim 9 in which the sample cell has a chamber for receiving the powder material, a wall or base of said chamber comprises a window through which scanning is to be effected, and said compacting means is arranged to compact the powder material against the window and to maintain said material under a predetermined compaction.

11. Apparatus according to claim 10 in which the compacting means comprises a plate-like component received within the chamber and resiliently biased for compacting the powder material between itself and the window.

12. Apparatus according to any one of claim 9 in which for control of said scanning the sample cell is displaceable longitudinally (L) relative to the beam and the beam is adjustable in its lateral width (W).

13. Apparatus according to claim 12 in which said longitudinal displacement (L) of the sample cell is through a stroke (L) which is adjustable in length.

14. Apparatus according to claim 9 and comprising a computer programmed to carry out the analysis of a powder material compacted to a predetermined density.

15. Use of a computer when programmed to carry out the analysis of a powder material compacted to a predetermined density according to claim 1.

16. Use of a spectrophotometric sample cell comprising a hollow body having a window through which spectrophotometric analysis by reflectance measurement of a powder material retained in the body is to be effected and means for compacting the powder material against said window and maintaining said material under a predetermined compaction pressure, for spectrophotometric analysis of said material, which use comprises compacting said powder material to a predetermined density, determining the penetration depth of a beam of electromagnetic radiation in the compacted material and scanning the compacted powder material by the beam of electromagnetic radiation over an area (W, L) and through a depth of the compacted material.

17. Use of a sample cell according to claim 16 wherein in said sample cell said hollow body provides a chamber in which the window is located and the compacting means comprises a component received within the chamber and resiliently biased relative to the body for compacting the powder material between itself and the window.

18. Use of a sample cell according to claim 17 wherein in said sample cell said compacting component comprises a pressure plate.

19. Use of a sample cell according to claim 17 wherein in said sample cell said compacting component is resiliently biased relative to the body by spring means.

20. Use of a sample cell according to claim 17 wherein in said sample cell said compacting component is carried by plate means relative to which it is resiliently biased and said plate means is removably secured to said hollow body.

* * * * *